(12) United States Patent
Suehira et al.

(10) Patent No.: US 8,517,537 B2
(45) Date of Patent: Aug. 27, 2013

(54) OPTICAL COHERENCE TOMOGRAPHIC IMAGING METHOD AND OPTICAL COHERENCE TOMOGRAPHIC IMAGING APPARATUS

(75) Inventors: Nobuhito Suehira, Kawasaki (JP); Kazuhiro Matsumoto, Yokohama (JP); Nobuhiro Tomatsu, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/286,481

(22) Filed: Nov. 1, 2011

(65) Prior Publication Data
US 2012/0188510 A1    Jul. 26, 2012

(30) Foreign Application Priority Data

Jan. 20, 2011  (JP) ................... 2011-009345
Jan. 20, 2011  (JP) ................... 2011-009347

(51) Int. Cl.
*A61B 3/14* (2006.01)
(52) U.S. Cl.
USPC .................... 351/208; 351/246; 382/131
(58) Field of Classification Search
USPC ............ 351/200–221, 246, 247; 250/363.05, 250/582, 583; 378/1–27, 62, 63; 382/128, 382/131
See application file for complete search history.

(56) References Cited

U.S. PATENT DOCUMENTS

| | | |
|---|---|---|
| 4,820,037 A | 4/1989 | Kohayakawa et al. |
| 4,848,896 A | 7/1989 | Matsumoto |
| 4,952,049 A | 8/1990 | Matsumoto |
| 5,076,274 A | 12/1991 | Matsumoto |
| 5,233,372 A | 8/1993 | Matsumoto |
| 5,455,644 A | 10/1995 | Yazawa et al. |
| 5,615,278 A | 3/1997 | Matsumoto |
| 5,847,805 A | 12/1998 | Kohayakawa et al. |
| 6,124,930 A | 9/2000 | Fercher |
| 6,158,864 A | 12/2000 | Masuda et al. |
| 6,273,565 B1 | 8/2001 | Matsumoto |
| 6,327,375 B1 | 12/2001 | Matsumoto et al. |
| 6,456,787 B1 | 9/2002 | Matsumoto et al. |
| 6,488,377 B2 | 12/2002 | Matsumoto |

(Continued)

FOREIGN PATENT DOCUMENTS

| | | |
|---|---|---|
| DE | 198 32 175 A1 | 1/1999 |
| JP | 2009-279031 A | 12/2009 |
| WO | 2009/120543 A1 | 10/2009 |

OTHER PUBLICATIONS

Oct. 16, 2012 European Communication in European Patent Appln. No. 11189104.0.

*Primary Examiner* — Darryl J Collins
*Assistant Examiner* — Gary O'Neill
(74) *Attorney, Agent, or Firm* — Fitzpatrick, Cella, Harper & Scinto

(57) ABSTRACT

In an OCT apparatus used in ophthalmology, if a working distance between an eye to be inspected and an objective lens varies, a shape of an obtained tomographic image is changed. This means that the OCT apparatus cannot be used for examining a variation of eyeball shapes. Provided is an optical coherence tomographic imaging method, including: acquiring a first distance between the eye to be inspected and the objective lens, corresponding to first tomographic image of the eye to be inspected; and correcting the first tomographic image to be second tomographic image corresponding to a second distance between the eye to be inspected and the objective lens, which is different from the first distance.

20 Claims, 6 Drawing Sheets

(56) References Cited

U.S. PATENT DOCUMENTS

| | | |
|---|---|---|
| 6,585,374 B2 | 7/2003 | Matsumoto |
| 6,779,890 B2 | 8/2004 | Matsumoto |
| 6,832,835 B2 | 12/2004 | Matsumoto |
| 2008/0170204 A1* | 7/2008 | Podoleanu .................. 351/206 |
| 2010/0182610 A1* | 7/2010 | Utsunomiya ................ 356/498 |
| 2010/0226553 A1 | 9/2010 | Suehira |
| 2010/0226554 A1 | 9/2010 | Suehira |
| 2010/0321700 A1 | 12/2010 | Hirose et al. |
| 2011/0007957 A1 | 1/2011 | Sakagawa |
| 2011/0051088 A1 | 3/2011 | Shimizu et al. |
| 2011/0058175 A1 | 3/2011 | Suehira |
| 2011/0096333 A1 | 4/2011 | Suehira et al. |
| 2011/0098560 A1 | 4/2011 | Suehira et al. |
| 2011/0299035 A1 | 12/2011 | Suehira |
| 2012/0002166 A1 | 1/2012 | Tomatsu et al. |
| 2012/0044499 A1 | 2/2012 | Shimoyama et al. |

* cited by examiner

OPTICAL COHERENCE TOMOGRAPHIC IMAGING METHOD AND OPTICAL COHERENCE TOMOGRAPHIC IMAGING APPARATUS

BACKGROUND OF THE INVENTION

1. Field of the Invention

The present invention relates to an optical coherence tomographic imaging method and an optical coherence tomographic imaging apparatus, and more particularly, to an optical coherence tomographic imaging method and an optical coherence tomographic imaging apparatus which are used for ophthalmologic diagnosis and treatment.

2. Description of the Related Art

Currently, there are used various types of ophthalmologic apparatus using an optical instrument. Examples of the optical instrument include an anterior ocular segment photographing device, a fundus camera, and a confocal scanning laser ophthalmoscope (SLO). Of those, an optical coherence tomographic imaging apparatus employing optical coherence tomography (OCT) which utilizes low coherence light is an apparatus capable of acquiring with a high resolution a tomographic image of an eye to be inspected, and is thus becoming an indispensable apparatus as the ophthalmologic apparatus in outpatient treatment specialized in retina. Hereinbelow, this apparatus is referred to as OCT apparatus.

A fundus observation apparatus described in Japanese Patent Application Laid-Open No. 2009-279031 includes a fundus camera unit, an OCT unit, and a calculation controller. The fundus camera acquires a two-dimensional image of a fundus, and the OCT unit acquires a tomographic image of the fundus. Further, it is possible to perform measurement by specifying a characteristic part of the fundus and changing an irradiation position of measurement light. Then, the tomographic image and a three-dimensional image of the fundus can be formed.

SUMMARY OF THE INVENTION

According to a first aspect of the present invention, there is provided an optical coherence tomographic imaging method for acquiring a tomographic image of an eye to be inspected based on combined light of return light from a retina of the eye to be inspected, which is irradiated with measurement light via an object lens, and reference light corresponding to the measurement light, the optical coherence tomographic imaging method including: acquiring the first distance between the eye to be inspected and the objective lens, corresponding to first tomographic image of the eye to be inspected; and correcting the first tomographic image corresponding to a second distance between the eye to be inspected and the objective lens, which is different from the first lens.

If a working distance that is an interval between the eye to be inspected and the objective lens is different, a shape of a retina in the tomographic image is also different. According to the first aspect of the present invention, a shape difference of the retina in the tomographic image due to a difference of the working distance can be reduced. Therefore, it is possible to provide a tomographic image that is suitable for observing variation with time of an eyeball shape or the like.

Further, according to a second aspect of the present invention, there is provided an optical coherence tomographic imaging method for acquiring a tomographic image of an eye to be inspected by adjusting a distance between the eye to be inspected and an objective lens and based on combined light of return light from the eye to be inspected and reference light, the return light being obtained by irradiating the eye to be inspected with measurement light, the optical coherence tomographic imaging method including: measuring the distance between the eye to be inspected and the objective lens; acquiring the tomographic image of the eye to be inspected; setting a region in the tomographic image in which a curvature is to be calculated; and calculating, by using the calculated distance, the curvature of the set region.

If a working distance that is an interval between the eye to be inspected and the objective lens is different, a shape of a retina in the tomographic image is also different. According to the second aspect of the present invention, a shape difference of the retina in the tomographic image due to a difference of the working distance can be reduced. Therefore, it is possible to quantitatively measure the shape of an eye, such as the curvature of the retina.

Further features of the present invention will become apparent from the following description of exemplary embodiments with reference to the attached drawings.

DESCRIPTION OF THE EMBODIMENTS

Hereinbelow, embodiments of the present invention are described in detail with reference to the drawings.

First Embodiment

Figure 1:
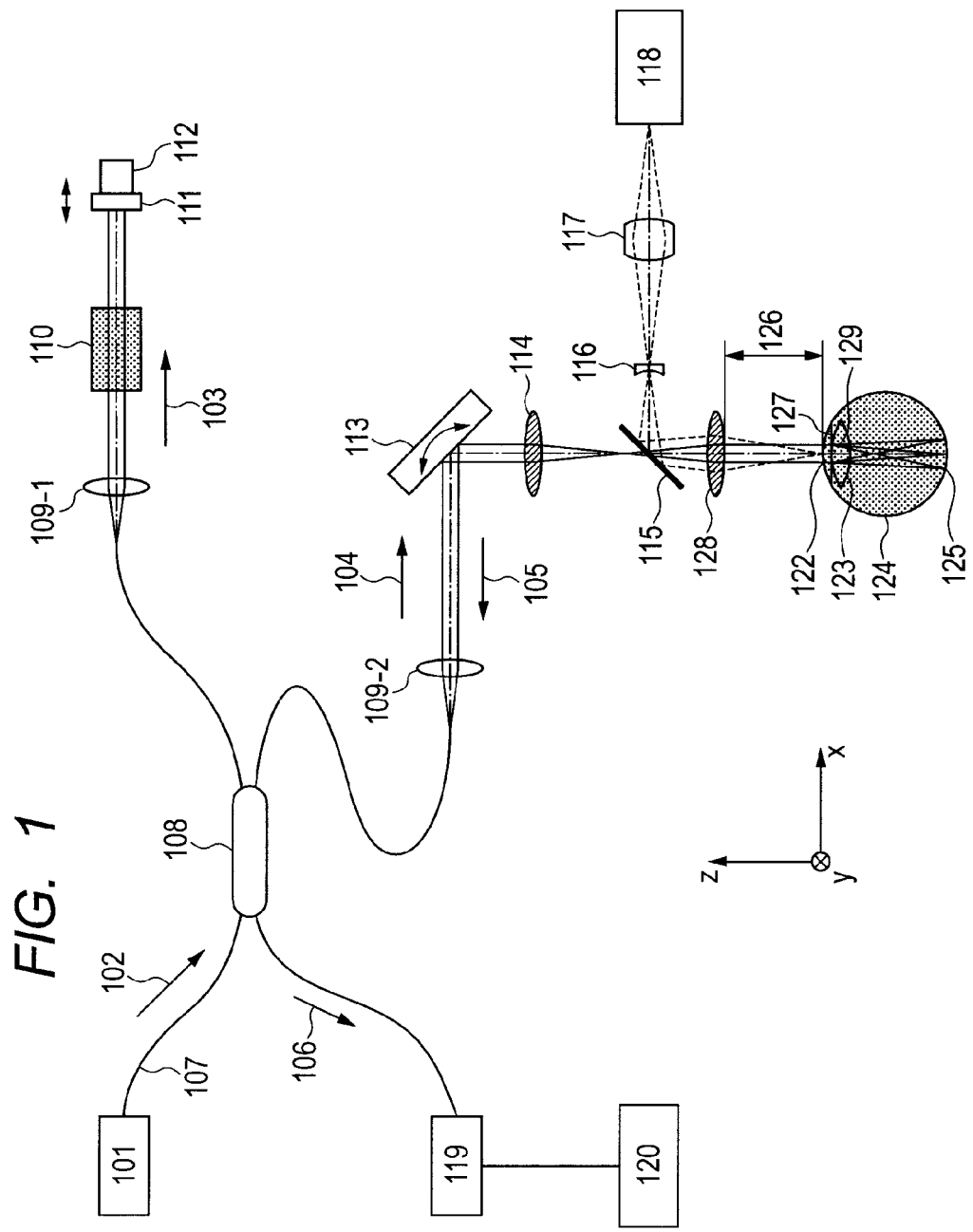
FIG. 1 is a diagram illustrating an OCT apparatus.

FIG. 1 is a diagram illustrating a structure of an optical coherence tomographic imaging apparatus according to a first embodiment of the present invention.

(Optical System)

The optical coherence tomographic imaging apparatus is formed by a Michelson interferometer. Exiting light 102 of a light source 101 is guided by a single mode fiber 107 so as to enter an optical coupler 108. The optical coupler 108 splits the light into reference light 103 and measurement light 104. Then, the measurement light 104 is reflected or scattered by a measurement part of a retina 125 to be observed and becomes return light 105 that comes back to the optical coupler 108. Then, the optical coupler 108 combines the return light 105 with the reference light 103 that has propagated through a reference optical path, which becomes combined light 106 and reaches a spectrometer 119.

The light source 101 is a super luminescent diode (SLD) that is a typical low coherence light source. Considering that the measurement light is used for measuring an eye, the wavelength of the near-infrared light is suitable for the wavelength thereof. Further, the wavelength affects the resolution of the acquired tomographic image in the lateral direction, and hence the wavelength is desirably as short as possible. In this embodiment, the central wavelength is 840 nm and the bandwidth is 50 nm. Depending on the measurement region to be observed, another wavelength may be selected as a matter of course. Note that, the light source of SLD type is used in this embodiment, but an amplified spontaneous emission (ASE) type or the like may be used as long as the light source emits low coherence light.

Next, the reference optical path of the reference light 103 is described. The reference light 103 split by the optical coupler 108 exits from a lens 109-1 after being substantially collimated. After that, the reference light 103 passes through dispersion compensation glass 110, and changes its direction by a mirror 111. Then, the reference light 103 is guided to the spectrometer 119 via the optical coupler 108 again. Note that, the dispersion compensation glass 110 compensates for dispersion of the measurement light 104 propagating forward and backward between an eye 124 to be inspected and a scan optical system, with respect to the reference light 103. Here, the length of the dispersion compensation glass 110 is set to 24 mm as a typical value supposing an average eyeball diameter of Japanese people. The optical path length of the reference light can be adjusted by adjusting the position of a coherence gate by moving an electric stage 112 in an arrow direction. The coherence gate is a position on the optical path of the measurement light to be the same distance as the optical path length of the reference light. The electric stage 112 is controlled by a computer 120.

Next, a measurement optical path of the measurement light 104 is described. The measurement light 104 split by the optical coupler 108 exits from a lens 109-2 after being substantially collimated and enters a mirror of an XY scanner 113 constituting the scan optical system. The XY scanner 113 is illustrated as a single mirror in FIG. 1, but actually includes two mirrors, which are disposed closely to each other, one for an X-scan mirror and the other for a Y-scan mirror. The measurement light reaches the eye 124 to be inspected via a lens 114, a dichroic mirror 115, and an objective lens 128.

Here, observation of an anterior ocular segment, namely a cornea 122 is described. As illumination light for observing the anterior ocular segment, a ring-like light source (not shown) outside the objective lens is used. This illumination light is reflected by the cornea 122, and the reflection light passes through the objective lens 128 again. The light is then reflected by the dichroic mirror 115 and reaches an observation system 118 via a split prism 116 and an optical system 117. Note that, the split prism 116 is disposed at a position conjugated with the cornea 122.

In addition, the objective lens 128 is disposed to be opposed to the eye 124 to be inspected, and shapes the measurement light that is guided to the eye 124 to be inspected.

(Working Distance)

Next, a working distance is described. Here, a working distance 126 is defined as a length (distance) between the surface of the cornea 122 and the surface of the objective lens 128. This length corresponds to a first distance in the present invention. First, an optical system of a general OCT apparatus is designed so that a pupil 129 of the eye 124 to be inspected becomes a scan rotation center of the measurement light 104.

Therefore, it is desired to perform the OCT measurement by adjusting a distance between the objective lens 128 and the eye 124 to be inspected so that the working distance takes a design value. However, the optical system of the OCT apparatus has a small NA and hence has a deep focal depth. As a result, even if the working distance is deviated from the design value, an image can be taken without a problem. Note that, if the working distance is greatly deviated from the design value, the light may be blocked by an iris 127 or focus may be blurred.

Figures 2A, 2B, 2C:
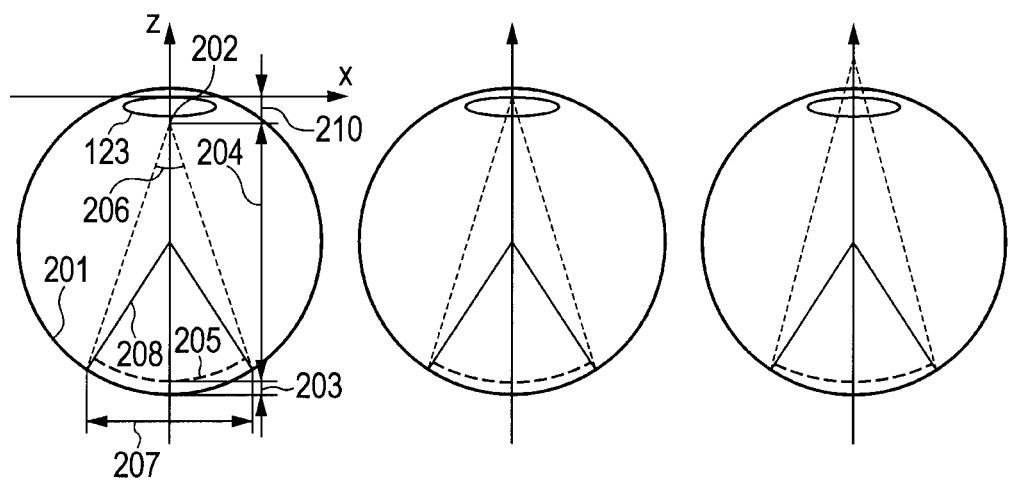
FIGS. 2A, 2B and 2C are diagrams illustrating a working distance and a scan radius.

Here, with reference to the schematic diagrams of an eye illustrated in FIGS. 2A to 2C, a relationship among the working distance, a rotation center 202 of the scan of the measurement light, and a locus 205 of the coherence gate is described. In those diagrams, the horizontal axis represents the x-axis of a first scan, and the vertical axis represents the z-axis in the depth direction. Then, the origin of the rotation center is supposed to be a position of the pupil as the design value. Note that, in those diagrams, the rotation center 202 is an intersection of light rays entering a retina 201 extended as they are, and is not an intersection of light rays refracted by the cornea or a crystalline lens 123.

The rotation center 202 of the scan of the measurement light moves as the working distance 126 varies. Further, a scan radius 204 and a scan angle 206 in the scan of the measurement light 104 are also varied along with the variation of the working distance 126. In addition, the XY scanner 113 includes two mirrors in many cases. For instance, it is supposed that the rotation center of the y-axis is on the objective lens side by, for example, 1 mm. In this case, it is necessary to correct the movement in the y-axis by three-dimensional measurement separately. Here, it is supposed that the rotation center is the same between the x-axis and the y-axis.

FIG. 2A illustrates a case where the rotation center 202 is on the side closer to the retina 201 with respect to the pupil 129 because the working distance 126 is smaller than the design value. As a matter of course, the distance between the rotation center 202 and the retina 201 becomes smaller than the design value. Note that, in the OCT measurement, the coherence gate is disposed on a corpus vitreum side so that the retina 201 can be observed. The position of the locus 205 of the coherence gate can be changed by a reference mirror 111. FIG. 2B illustrates a case where the working distance 126 is substantially the same as the design value. The distance between the rotation center 202 and the retina 201 is the design value. FIG. 2C illustrates a case where the working distance 126 is longer than the design value and the rotation center 202 is disposed at a position closer to the objective lens 128 with respect to the pupil 129.

As illustrated in FIGS. 2A to 2C, as the scan radius 204 becomes longer, the locus becomes flattened. In other words, in the OCT apparatus, a difference between the retina 201 and the locus 205 of the coherence gate is displayed as an image. Therefore, as the scan radius 204 becomes longer, an apparent curvature becomes larger. However, there are characteristics that light rays entering at the same angle with respect to the optical axis form images at the same position in the eyeball even if the working distance 126 varies. Therefore, a scan range 207 is not changed so much.

Further, a relationship between the distance variation of the working distance 126 and the position of the rotation center 202 is described. Note that, a difference 210 of the working distance 126 from the design value is represented by a variable g as the space distance. Because the origin is the pupil 129, the variable g has a value in the z-axis. In addition, a reference working distance corresponds to a second distance in the present invention and is the design value (g=0), for example. Here, the space distance between the rotation center 202 and the retina 201 is expressed by f(g) using the variable g. In addition, the coherence gate is based on a retina position of a standard eye as a reference and is specifically at a position of 24 mm from the pupil. A difference 203 from this reference on the z-axis is represented by a variable s as the space distance. Using those, the scan radius 204 L(g) is expressed by Expression 1.

$$L(g)=f(g)-s \qquad \text{Ex. 1}$$

The movement of the coherence gate is converted into a movement amount ΔM of the reference mirror 111 and is expressed by Expression 2 using the refractive index $n_h$ of the eye to be inspected.

$$\Delta M = n_h s \qquad \text{Ex. 2}$$

Figure 3:
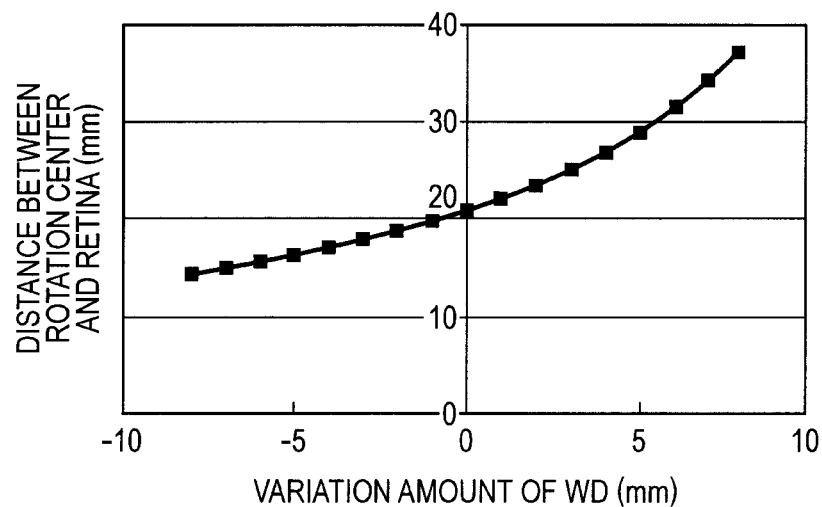
FIG. 3 is a graph illustrating a relationship between the working distance and a distance between a rotation center and a retina.

Here, the variation of the space distance f(g) between the rotation center 202 and the retina 201 is not proportional to the variation of the working distance 126. The reason is that the cornea 122 and the crystalline lens 123 cause refraction. FIG. 3 illustrates a result of simulation of the space distance f(g) between the rotation center 202 and the retina 201. The horizontal axis represents a variation amount g of the working distance 126 from the design value. The vertical axis represents the space distance between the rotation center 202 and the retina 201. It is understood that if the working distance 126 is negative, the movement of the rotation center is smaller than the variation of the working distance 126. It is understood that if the working distance 126 is positive on the contrary, the movement of the rotation center is larger than the variation of the working distance 126. In this simulation, a model having an axial length of 24 mm was used. If the axial length changes, f(g) also changes as a matter of course. In this case, it is necessary to perform the simulation for each axial length model. In addition, if the rotation center is different between the x-axis and the y-axis, another simulation is necessary.

Figure 4:
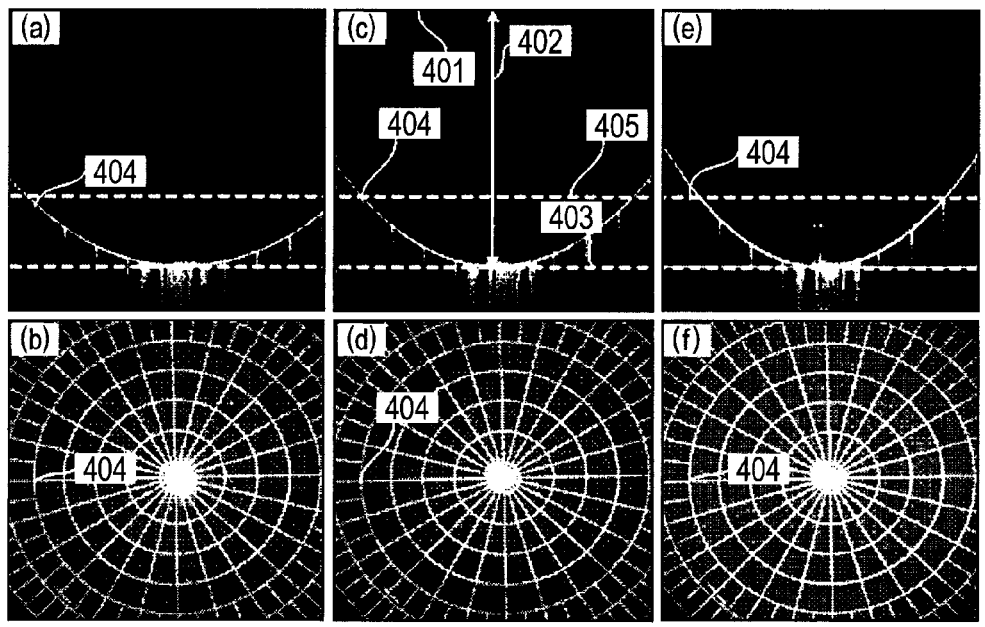
FIG. 4 is diagram illustrating variations of a tomographic image and a two-dimensional image due to a variation of the working distance.

Here, an example in which a model eye was imaged with the OCT apparatus is described with reference to (a) to (f) of FIG. 4. This model eye has radial and circular patterns disposed at a part corresponding to the retina. The part corresponding to the retina is on the surface of the glass. Those images were taken by changing the working distance 126 and adjusting so that the vertex of the retina position of the model eye had the same distance from the coherence gate in the tomographic images. (a) of FIG. 4 illustrates the tomographic image in a case where the working distance 126 is shorter than the design value by 4 mm, and (b) of FIG. 4 illustrates a two-dimensional projection image thereof. (c) of FIG. 4 illustrates the tomographic image in a case where the working distance 126 is the design value, and (d) of FIG. 4 illustrates a two-dimensional projection image thereof. (e) of FIG. 4 illustrates the tomographic image in a case where the working distance 126 is longer than the design value by 4 mm, and (f) of FIG. 4 illustrates a two-dimensional projection image thereof. Note that, in the tomographic images, the retina of the model eye is imaged as arcs of different curvatures. In addition, concentric circles and radial lines of the projection image are projection of the imaged concentric circles and radial lines of the model eye in the retina position. Focusing on an intersection 404 between a circle and a straight line, an additional line 405 is drawn in the corresponding tomographic image. It is understood that the image of the retina is moved to the lower side of the additional line in (a) of FIG. 4 and to the upper side thereof in (e) of FIG. 4. However, the measurement range is not substantially changed as illustrated in (b), (d) and (f) of FIG. 4.

Figure 5A:
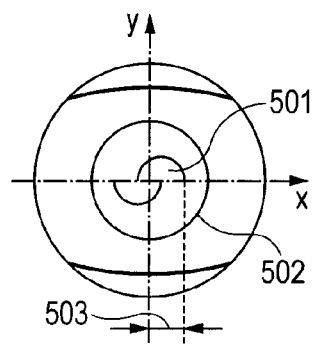
FIGS. 5A, 5B and 5C are diagrams illustrating a variation of anterior ocular segment observation due to a variation of the working distance.
Figure 5B:
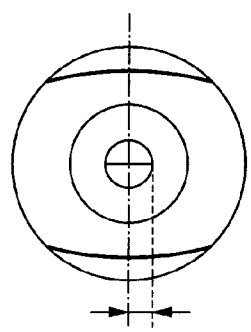
Figure 5C:
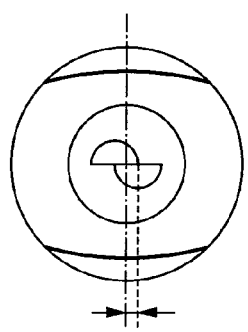

Next, measurement of the working distance is described with reference to FIGS. 5A to 5C. FIGS. 5A to 5C illustrate images of the cornea taken by the observation system 118 of the anterior ocular segment, in which a pupil 501 and an iris 502 are observed. It is designed that an image of the pupil 501 is split by a beam splitter prism into a positive region and a negative region in the y direction on both sides of the x-axis so as to be formed in the observation system 118. FIG. 5A illustrates a case where the working distance 126 is shorter than the design value, FIG. 5B illustrates a case where the working distance 126 is substantially the same as the design value, and FIG. 5C illustrates a case where the working distance 126 is longer than the design value. If the working distance 126 is substantially the same as the design value, the pupil 501 becomes an image that is not split. On the other hand, if the working distance 126 is shorter than the design value, the upper image of the pupil is moved to the right side. If the working distance 126 is longer than the design value, the upper image of the pupil is moved to the left side. By measuring a difference 503 between the upper and lower images of the pupil 501, the length of the working distance 126 can be known.

The working distance 126 corresponds to the above-mentioned first distance in the present invention. The structure for knowing the length of the working distance 126 described above corresponds to a unit of adjusting and measuring the first distance in the present invention together with the structure of adjusting a position of the objective lens 128 (not shown). Alternatively, the structure for knowing the length of the working distance 126 corresponds to an acquiring unit that acquires a first distance between the objective lens and the eye to be inspected corresponding to first tomographic image of the present invention.

Note that, the distance between the rotation center and the retina can be known by measuring the working distance 126 and the movement amount of the mirror 111. In other words, if the coherence gate is set to a position of the design value and coincides with the retina, it is found that the axial length is 24 mm as designed. If the position does not coincide with the retina, the coherence gate is moved so as to search for a position that coincides with the retina. From this movement amount, the true axial length can be known. Note that, the retina has a thickness, and, for example, a boundary between the corpus vitreum and the nerve fiber layer is regarded as the design value.

(Signal Processing)

Figure 6:
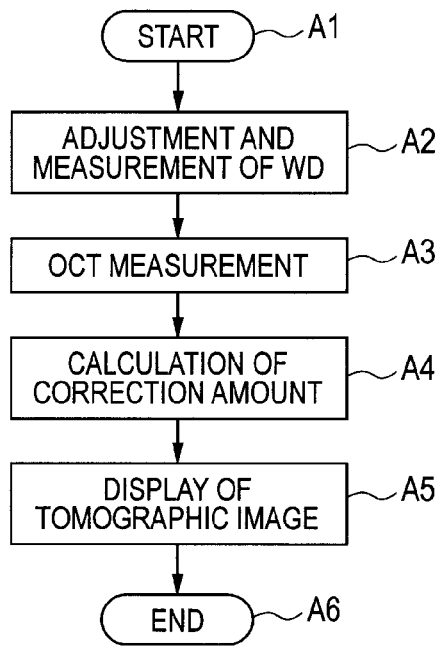
FIG. 6 is a diagram illustrating a procedure of signal processing in a first embodiment of the present invention.

Now, signal processing of the OCT measurement is described with reference to FIG. 6.

In Step A1, measurement is started. In this state, the OCT apparatus is in operation, and the eye to be inspected is disposed at a measurement position.

In Step A2, adjustment and measurement of the working distance (WD) 126 are performed. Here, the position of the pupil is regarded as the origin of the coordinate system. Alignment is performed while observing the cornea 122 with the anterior ocular segment observation system 118. The working distance 126 is adjusted so as to be in a range of ±5 mm of the design value as a target. If the curvature is large in particular, specifically if a value of the curvature is larger than a predetermined value, the objective lens may be closer to the eye to be inspected in the range where the measurement light is not blocked by the iris or the like. This is an operation of disposing a unit for measuring the curvature to bring the objective lens to be closer to the eye to be inspected in accordance with the measured value. By adding this operation, an appropriate tomographic image can be obtained even for the eye to be inspected having a large curvature of the retina so as to perform Step A3 and subsequent steps. Note that, the negative direction means a direction in which the objective lens approaches the cornea. As a matter of course, positions of the coherence gate and focus are adjusted together with adjustment of the working distance.

In Step A3, the OCT measurement is performed. The scan range 207 is, for example, a range of 6 mm for imaging macula lutea or a range of 10 mm for imaging macula lutea and mamilla. Here, in order to take an image in a range of 6 mm, data including 512 lines in the x direction and 512 lines in the y direction is acquired. One-dimensional array line data (1,024 pixels) is acquired for each line from the spectrometer 119 and are sent sequentially to the computer 120. Then, the data of 512 lines that are continuous in the x direction is stored in units of two-dimensional array data. The data size is 1,024× 512×12 bits. As a result, 512 data is generated in the y direction.

A tomographic image (B-scan image) can be obtained from the measured two-dimensional array data after fixed noise reduction, wavelength-wavenumber conversion, Fourier transformation, and the like are performed. This tomographic image is checked. If it is determined that a desired measurement was achieved, the eye to be inspected is removed from the measurement position. The above-mentioned structure for performing the OCT measurement corresponds to the unit for acquiring information for generating a tomographic image of the eye to be inspected constituted of a plurality of line data in the present invention.

Figure 7A:
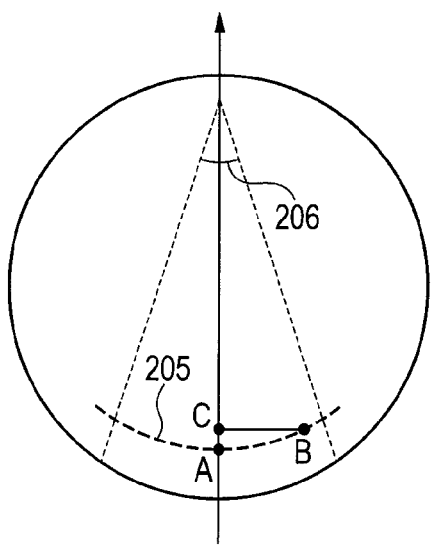
FIGS. 7A and 7B are conceptual diagrams of a correction amount.

Next, a correction amount is calculated in Step A4. First, a general tomographic image is displayed relatively with reference to a position of the coherence gate. However, as illustrated in FIG. 7A, the locus 205 of the coherence gate forms an arc of a sector. When a point B is on a j-th line scan, a point C is the projection on the z-axis. A variation amount d(g) indicating how much the coherence gate varies with respect to a point A on the z-axis is expressed by Expression 3. Here, using the scan angle (θ(g)) 206 when the working distance is different from the design value by g, the scanner rotates by θ(g)/(N−1) at a time. In addition, j denotes an integer of 0 to N−1, and N denotes the number of lines in the x direction, that is, 512.

$$d_j(g) = L(g)\left(1 - \cos\left(\frac{\theta(g)}{N-1}\left(\frac{N-1}{2} - j\right)\right)\right) \quad \text{Ex. 3}$$

Note that, the scan angle 206 and the distance f(g) between the rotation center 202 and the retina 201 viewed from the retina 201 are varied due to the variation of the working distance 126, but the scan range 207 (W) is not changed substantially. Therefore, the scan angle θ(g) viewed from the retina 201 has a relationship expressed in Expression 4. As a matter of course, it is possible to determine θ(g) by the simulation.

$$f(g)\sin\left(\frac{\theta(g)}{2}\right) = \frac{W}{2} \quad \text{Ex. 4}$$

f(g) may be simulated in advance as illustrated in FIG. 3, and hence $d_j(g)$ can be determined. By using the expression for determining the variation amount $d_j(g)$, it is possible to correct each of the above-mentioned line data. Step A4 is performed by the computer 120. The computer 120 corresponds to a unit for calculating a correction amount in each of a plurality of line data in the present invention. As described above, in Step A3, the correction amount of each of the line data is determined based on a first distance (g) between the eye to be inspected and the objective lens, a distance (f(g)) between the rotation center and the retina in the scan viewed from the retina that is scanned with the measurement light, the scan angle (θ(g)) in the scan with the measurement light viewed from the retina, and the coherence gate position (s) determined by the optical path length of the reference light.

Figure 7B:
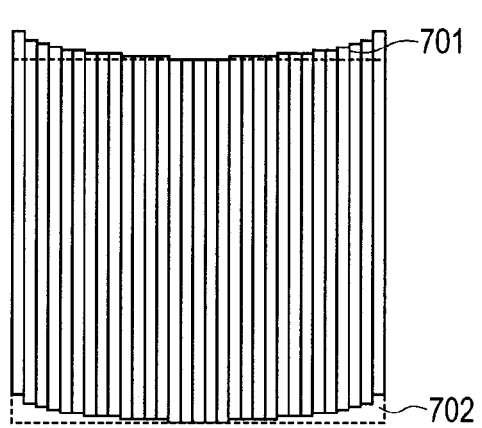

Further, a tomographic image is generated in Step A5. Because Expression 3 expresses the space distance, the refractive index $n_h$ is multiplied, and then division by a pixel resolution is performed so as to calculate the number of pixels to be shifted. FIG. 7B illustrates a conceptual diagram in which each line 701 is corrected by the determined correction amount. This example shows a case where the working distance is shorter than the design value, and shows that the entire imaging range indicated by a dot line is extracted as an image with reference to the line in the center part. Noise level data is added to a part 702 without data. If excess data is calculated in the depth direction, the data is used to fill up. As a matter of course, the working distance to be the reference may not be the design value but another value.

The process ends in Step A6. The process ends after confirming that desired data is obtained. Note that, the above-mentioned steps for generating a tomographic image are performed by the computer 120, which corrects the first tomographic image to second tomographic image corresponding to the second distance that is different from the above-mentioned first distance and is the reference working distance between the eye to be inspected and the objective lens. This structure corresponds to a correction unit in the present invention.

As a result, even if the working distance is different from the design value, an image of the reference working distance can be generated. In other words, even if the person has a large curvature, an image having relatively the same working distance can be obtained by performing the measurement considering the curvature.

Note that, as described above, the measurement light scans the retina with the x-scanner and the y-scanner having different rotation axes, namely rotation centers. Therefore, it is necessary to perform the correction of the tomographic image in consideration of a positional difference between the rotation centers of the scanners. In the present invention, in the A4 step, it is possible to generate a tomographic image in which the difference of the rotation center is reflected on the working distance. Thus, it is possible to obtain a more appropriate tomographic image in an actual OCT apparatus.

As described above, according to this embodiment, adjustment and measurement of the working distance between the eye to be inspected and the objective lens are performed so as to correct the image. Thus, a difference in shape due to a difference of working distance can be reduced. In addition, even if the eye to be inspected has a large curvature, the obtained tomographic image can be used for analyzing the shape. In addition, because it is not necessary to adjust the working distance to the design value in the imaging, measurement time can be shortened.

Second Embodiment

Figure 8:
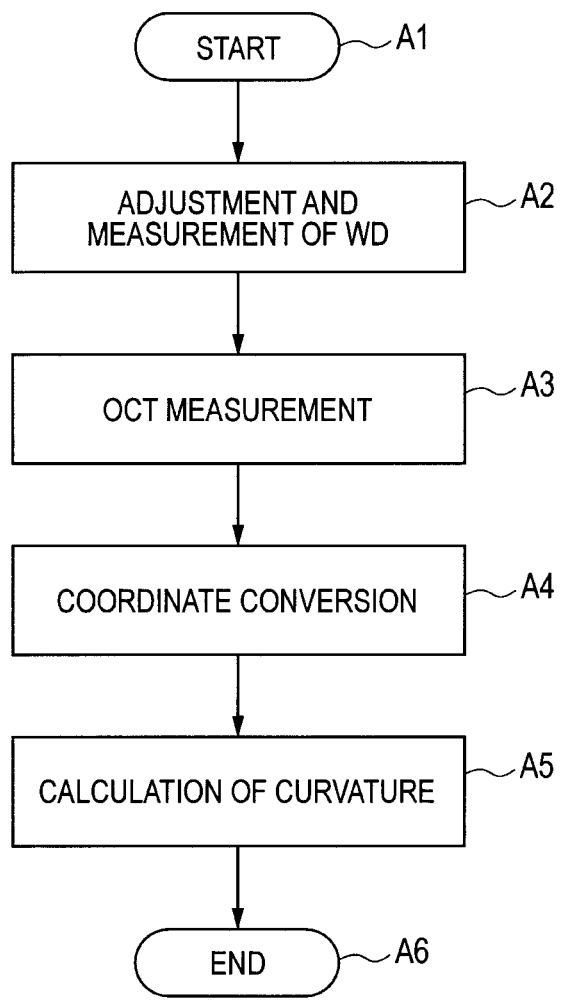
FIG. 8 is a diagram illustrating a procedure of signal processing in a second embodiment of the present invention.

Now, signal processing of the OCT measurement according to a second embodiment of the present invention is described with reference to FIG. 8.

In Step A1, measurement is started. In this state, the OCT apparatus is in operation, and the eye to be inspected is disposed at a measurement position.

In Step A2, adjustment and measurement of the working distance (WD) 126 are performed. First, alignment between the OCT apparatus and the eye to be inspected is performed while observing the cornea 122 with the anterior ocular segment observation system 118. The working distance 126 is adjusted so as to be in a range of ±5 mm of the design value as a target. Note that, if the curvature is large, the objective lens may be closer to the eye to be inspected in the range where the measurement light is not blocked by the iris. As a matter of course, positions of the coherence gate and the focus are adjusted together with the adjustment of the working distance. Note that, the axial length can be measured by another apparatus, but the OCT apparatus is used for the measurement at this stage if necessary. In other words, the coherence gate is moved in the state where the working distance 126 is measured, and a boundary between the corpus vitreum and the nerve fiber layer is searched for. Further, a position of the coherence gate at this time point is stored. The position of the coherence gate can be measured by an encoder (not shown). Note that, as described above, the OCT apparatus corresponds to an image acquiring unit that acquires a tomographic image of the eye to be inspected in the present invention.

The OCT measurement is performed in Step A3 so that a tomographic image of the eye to be inspected is acquired. The scan range 207 is, for example, a range of 6 mm for imaging macula lutea or a range of 10 mm for imaging macula lutea and mamilla. Here, in order to take an image in a range of 6 mm, data including 512 lines in the x direction and 512 lines in the y direction are acquired. One-dimensional array data (1,024 pixels) is acquired for each line from the spectrometer 119 and is sent sequentially to the computer 120. Then, the data of 512 lines that are continuous in the x direction is stored in units of two-dimensional array data. The data size is 1,024× 512×12 bits. As a result, 512 data is generated in the y direction.

A tomographic image (B-scan image) can be obtained from the measured two-dimensional array data after fixed noise reduction, wavelength-wavenumber conversion, Fourier transformation, and the like are performed. This tomographic image is checked. If it is determined that a desired measurement was achieved, the eye to be inspected is removed from the measurement position.

Figure 9A:
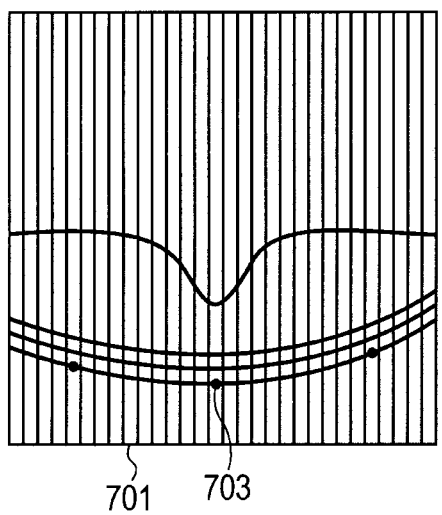
FIGS. 9A and 9B are diagrams illustrating coordinate conversion.
Figure 9B:
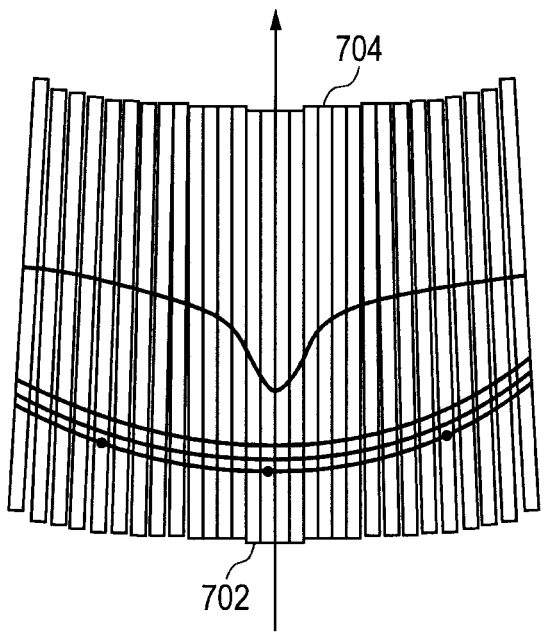

In Step A4, coordinate conversion from the tomographic image to space coordinates is performed for calculating the curvature. In this case, a region or a part in which the curvature is to be determined is set in advance. This setting is described with reference to FIGS. 9A and 9B. FIG. 9A illustrates a tomographic image of the eye to be inspected, and a size thereof is 500 (depth)×512 (lateral)×12 bits. A usual tomographic image is displayed so that the coherence gate 701 is aligned in a straight line. However, the position of the coherence gate is on the arc of a sector as illustrated in FIGS. 2A to 2C. In other words, when the tomographic image is converted into the space coordinates, the image needs to be disposed on a sector plane 702 as illustrated in FIG. 9B. Therefore, in order to calculate the curvature, this coordinate conversion is necessary. First, the coordinate conversion for a point in the i-th row and the j-th column in the tomographic image is considered. Here, i and j are integers in the range of 0 to 511.

Because the positions of the i-th row have the same distance from the coherence gate, the positions can be expressed by the formula of a circle. Therefore, the curve is expressed as follows using the pixel resolution h and the refractive index $n_h$. Note that, the 0th row 704 is a position of the coherence gate.

$$x^2 + z^2 = \left\{ L(g) + \frac{i \cdot h}{n_h} \right\}^2 \quad \text{Ex. 5}$$

It is supposed that the scanner is symmetric with respect to the z-axis and that the sampling is performed by a uniform interval of the scan angle symmetrically with respect to the z-axis. Then, the equation of a straight line of the j-th column is expressed by Expression 6 using N. Here, N is 512.

$$x - z \tan\left\{ \theta(g) \left( \frac{N - 2j - 1}{2N - 2} \right) \right\} = 0 \quad \text{Ex. 6}$$

Note that, the scan radius 204 and the scan angle 206 viewed from the retina 201 are varied due to the variation of the working distance 126, but the scan range 207 (W) is not changed substantially. Therefore, the scan angle θ(g) viewed from the retina 201 has a relationship expressed in Expression 7.

$$f(g) \sin\left( \frac{\theta(g)}{2} \right) = \frac{W}{2} \quad \text{Ex. 7}$$

The scan range W is a range of 6 mm, for example. Because f(g) is determined in advance by simulation or the like, θ(g) can be determined. As a matter of course, it is possible to determine θ(g) by simulation.

By using those, a position in the space coordinates can be expressed by Expressions 8 and 9.

$$x = -\left( L(g) + i \cdot \frac{h}{n_h} \right) \sin\left\{ \theta(g) \frac{N - 2j - 1}{2N - 2} \right\} \quad \text{Ex. 8}$$

$$z = -\left( L(g) + i \cdot \frac{h}{n_h} \right) \cos\left\{ \theta(g) \frac{N - 2j - 1}{2N - 2} \right\} \quad \text{Ex. 9}$$

Next, the region or the part where the curvature is to be calculated is extracted and converted by the coordinate conversion. Here, the curvature radius is determined from three points on a retinal pigment epithelium. The individual points are represented by $A_1 (x_1, z_1)$, $A_2 (x_2, z_2)$, and $A_3 (x_3, z_3)$. The point to be extracted may be selected automatically or may be selected by operator's designation on the displayed tomographic image. As a matter of course, such region may be a predetermined region in the retina, or a layer such as a choroid, a retinal pigment epithelium layer (RPE), an IS/OS (junction surface between inner segment and outer segment), an external limiting membrane (ELM), an outer nuclear layer (ONL), an outer plexiform layer (OPL), an inner nuclear layer (INL), an inner plexiform layer (IPL), a ganglion cell layer (GCL), a nerve fiber layer (NFL), or a boundary between the layers. Setting of the region or the part where the curvature is calculated is performed by a setting unit that sets the region for calculation, corresponding to the computer 120 for controlling various structures of the present invention.

In Step A5, the curvature is calculated. This is concluded by determining a radius of a circle passing through the points $A_1$, $A_2$, and $A_3$. In this case, an intersection of a perpendicular bisector of the side $A_1 A_2$ and a perpendicular bisector of the side $A_2 A_3$ becomes the center. The perpendicular bisector of the side $A_1 A_2$ is expressed by Expression 10.

$$\left(z - \frac{z_1 + z_2}{2}\right) = -\frac{x_2 - x_1}{z_2 - z_1}\left(x - \frac{x_1 + x_2}{2}\right) \quad \text{Ex. 10}$$

In addition, the perpendicular bisector of the side $A_2A_3$ is expressed by Expression 11.

$$\left(z - \frac{z_2 + z_3}{2}\right) = -\frac{x_3 - x_2}{z_3 - z_2}\left(x - \frac{x_2 + x_3}{2}\right) \quad \text{Ex. 11}$$

Therefore, the center $(x_c, z_c)$ of the circle is obtained by solving the expressions and is expressed by Expressions 12 and 13.

$$x_c = \frac{1}{2}\frac{(x_2^2 - x_1^2)z_3 + (x_1^2 - x_3^2)z_2 + (x_3^2 - x_2^2)z_1}{(x_2 - x_1)z_3 + (x_1 - x_3)z_2 + (x_3 - x_2)z_1} \quad \text{Ex. 12}$$

$$(z_2 - z_1)(z_3 - z_2)(z_1 - z_3) +$$

$$z_c = \frac{1}{2}\frac{(z_2^2 - z_1^2)x_3 + (z_1^2 - z_3^2)x_2 + (z_3^2 - z_2^2)x_1}{(z_2 - z_1)x_3 + (z_1 - z_3)x_2 + (z_3 - z_2)x_1} \quad \text{Ex. 13}$$

$$(x_2 - x_1)(x_3 - x_2)(x_1 - x_3) +$$

As a result, the curvature radius 208 (r) is a distance between the center of the circle and one of the points $A_1$, $A_2$, and $A_3$, and therefore can be determined by Expression 14.

$$r = \sqrt{(x_1 - x_c)^2 + (z_1 - z_c)^2} \quad \text{Eq. 14}$$

The curves calculated by using those expressions are superimposed and displayed on the tomographic image. In addition, the computer 120 performing the calculation corresponds to a calculation unit that calculates the curvature of the region set by using the working distance measured in the present invention. Note that, the display superimposed on the tomographic image having a curve based on the calculated curvature is performed by the computer 120 and a display apparatus (not shown), and those structures correspond to the display unit in the present invention.

Note that, Expression 14 indicates a circle passing through three points and the result may be deviated from the RPE when being displayed to overlay on the tomographic image. If there is a problem, the three points are set again for the calculation by narrowing the range.

As a matter of course, the region may be divided into some regions to determine a local curvature. Further, it is possible to determine the curvature in each region of a three-dimensional tomographic image so as to generate a two-dimensional map and to display the map (map display). The map display is performed by the computer 120 and a display apparatus (not shown), and those structures correspond to a map display unit in the present invention, which displays the curvature as a map. In addition, the determined curvature may be compared with a standard curvature.

The process ends in Step A6. The process ends after confirming that desired data is obtained.

As described above, according to this embodiment, a shape of the eye, in particular, a curvature of the retina can be measured accurately by measuring the working distance and the movement amount of the reference mirror.

Third Embodiment

Hereinafter, a third embodiment of the present invention is described with reference to the drawings. Here, a method of determining the curvature in a simplified manner is described.

Figure 10A:
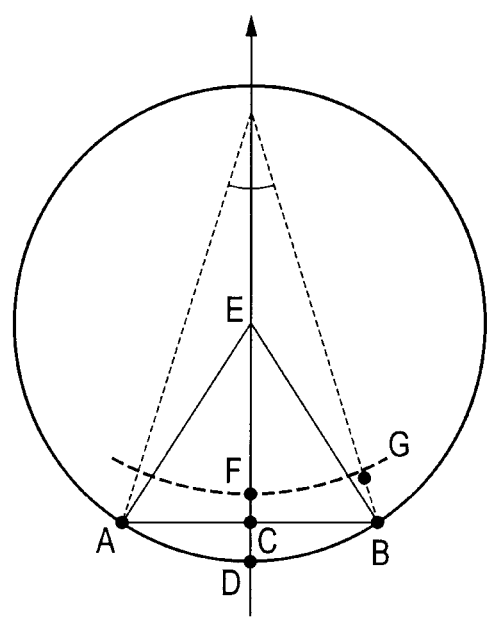
FIGS. 10A and 10B are diagrams illustrating calculation of curvature in a third embodiment of the present invention.
Figure 10B:
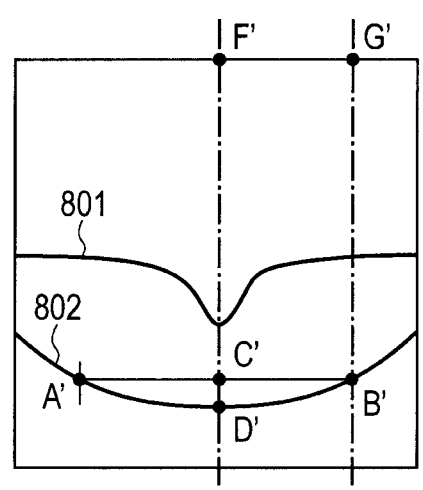

FIG. 10A schematically illustrates the space distance between the eye to be inspected and the measurement system. Here, the region in which a curvature radius is to be calculated is a retinal pigment epithelium 802. FIG. 10B illustrates a tomographic image of the eye to be inspected that is obtained by this arrangement and schematically illustrates a surface 801 of the nerve fiber layer and the retinal pigment epithelium 802. The point A and the point B have the same depth of the retinal pigment epithelium 802. The point C is an intersection of the perpendicular bisector of the side AB and the line AB, and the point D is an intersection of the perpendicular bisector of the side AB and the retinal pigment epithelium 802. The point F is an intersection of the coherence gate and the perpendicular bisector of the side AB. The point G is an intersection of the coherence gate and the straight line connecting the point B and the rotation center. In other words, the calculation of curvature is performed by using information including at least a bottom side and a height of a triangle constituted of two points having the same depth and a point on its perpendicular bisector in the tomographic image, and a coherence gate position determined by the optical path length of the reference light. In FIG. 10B, the corresponding point is indicated as A'. Here, supposing that BC=u, CD=v, and BE=r hold, a relationship of Expression 15 is satisfied.

$$(r-v)^2 + u^2 = r^2 \quad \text{Ex. 15}$$

This expression is solved for the curvature radius r, and Expression 16 is obtained.

$$r = \frac{u^2 + v^2}{2v} \quad \text{Ex. 16}$$

In order to determine the curvature radius r, it is necessary to know values of u and v. Here, u corresponds to the side B'C', which should be measured. By proofreading in advance using a model eye or the like, u can be easily known by counting the number of pixels. Next, as to v, because the positions of the coherence gate are aligned as a straight line in the tomographic image as illustrated in FIG. 9A, correction in the z direction is necessary. In other words, a difference with F is generated when G is projected to the z-axis. When the correction amount is denoted by d, a relationship of Expression 17 is obtained, supposing that the side F'C' is an optical distance p and that B' is on the q-th column.

$$d = \left(L(g) + \frac{p}{n_h}\right)\left(1 - \cos\left(\theta(g)\frac{N - 2q - 1}{2N - 2}\right)\right) \quad \text{Ex. 17}$$

When an optical distance of the side C'D' is denoted by T, a relationship of Expression 18 is obtained. Note that, T is a multiple of the pixel resolution of the tomographic image and the number of pixels.

$$T = n_h(v - d) \quad \text{Ex. 18}$$

Using those relationships, an approximation value of the curvature radius r can be determined.

Note that, as described above, the measurement light scans the retina with the x-scanner and the y-scanner having different rotation axes, namely rotation centers. Therefore, it is necessary to correct the tomographic image considering a positional difference between the rotation centers of those scanners. In the present invention, in the fourth step, it is also possible to generate a tomographic image in which the difference of the rotation center is reflected on the working distance. Thus, in the actual OCT apparatus, a more appropriate tomographic image can be obtained.

As described above, according to this embodiment, a curvature of the eye to be inspected can be determined in a simplified manner.

Other Embodiments

Further, the present invention is also implemented by executing the following processing. Specifically, in this processing, software (program) for implementing the functions of the above-mentioned embodiments is supplied to a system or an apparatus via a network or various kinds of storage medium, and a computer (or CPU, MPU, etc.) of the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-009345, filed Jan. 20, 2011, and Japanese Patent Application No. 2011-009347, filed Jan. 20, 2011 which are hereby incorporated by reference herein in their entirety.

What is claimed is:

1. An image acquiring method for acquiring a tomographic image of an eye to be inspected based on combined light of (a) return light from the eye to be inspected, which is irradiated with measurement light via an objective lens, and (b) reference light corresponding to the measurement light, the image acquiring method comprising:
acquiring a first tomographic image of the eye to be inspected at a first distance between the eye to be inspected and the objective lens; and
correcting a curvature of the first tomographic image based on the first distance.

2. An image acquiring method according to claim 1, further comprising calculating a correction amount for each of a plurality of line data of the first tomographic image based on the first distance,
wherein the correction amount is calculated using (a) the first distance, (b) a distance between a retina of the eye to be inspected and a scan rotation center viewed from the retina when the measurement light scans the retina, (c) a scan angle viewed from the retina when the measurement light scans, and (d) a coherence gate position determined by an optical path length of the reference light.

3. An image acquiring method according to claim 2, further comprising correcting the curvature of the first tomographic image based on a positional difference between the rotation centers of two scanners which are different rotation centers for scanning the measurement light respectively.

4. An image acquiring method according to claim 1, wherein a curvature of a retina of the eye to be inspected is measured, and when the curvature is larger than a predetermined value, the first distance is changed to a second distance which is shorter than the first distance, to thereby acquire a second tomographic image.

5. An image acquiring method for acquiring a tomographic image of an eye to be inspected by adjusting a distance between the eye to be inspected and an objective lens and based on combined light of (a) return light from the eye to be inspected and (b) reference light, the return light being obtained by irradiating the eye to be inspected with measurement light, the image acquiring method comprising:
measuring the distance between the eye to be inspected and the objective lens;
calculating, by using the distance, a curvature of a predetermined region in the tomographic image of the eye to be inspected; and
correcting the curvature of the predetermined region in the tomographic image based on the measured distance.

6. An image acquiring method according to claim 5, wherein the region comprises one of a choroid, a pigment epithelium layer, a junction surface between an inner segment and an outer segment, an external limiting membrane, an outer nuclear layer, an outer plexiform layer, an inner nuclear layer, an inner plexiform layer, a ganglion cell layer, a nerve fiber layer, and a boundary between the layers.

7. An image acquiring method according to claim 5, wherein the calculating of a curvature includes calculating the curvature by using all of (a) a distance between a scan rotation center of the measurement light and a retina, (b) a scan angle, (c) a coherence gate position determined by an optical path length of the reference light, (d) coordinates on the tomographic image, and (e) a pixel resolution of the tomographic image in a depth direction.

8. An image acquiring method according to claim 7, further comprising providing two scanners having different rotation centers for scanning the measurement light,
wherein the calculating of a curvature includes correcting a positional difference between the rotation centers of the two scanners before calculating the curvature.

9. An image acquiring method according to claim 5, wherein the curvature is calculated by using information including at least a bottom side and a height of a triangle formed of two points having the same depth and a point on its perpendicular bisector in the tomographic image, and a coherence gate position determined by an optical path length of the reference light.

10. An image acquiring method according to claim 5, further comprising controlling a display unit to display a curve determined based on the curvature on the tomographic image.

11. An image acquiring method according to claim 5, further comprising controlling a display unit to display curvatures calculated for a plurality of regions of the tomographic image as a map.

12. An image acquiring apparatus for acquiring a tomographic image of an eye to be inspected based on combined light of (a) return light from the eye to be inspected, which is irradiated with measurement light via an objective lens, and (b) reference light corresponding to the measurement light, the image acquiring apparatus comprising:
an acquiring unit for acquiring a first tomographic image of the eye to be inspected at a first distance between the eye to be inspected and the objective lens; and
a correction unit for correcting a curvature of the first tomographic image based on the first distance.

13. An image acquiring apparatus according to claim 12, further comprising a spectrometer for acquiring a plurality of line data for generating the tomographic image and sending the plurality of line data to the correction unit.

14. An image acquiring apparatus according to claim 12, further comprising a unit for moving the objective lens to adjust the first distance.

15. An image acquiring apparatus according to claim 12, further comprising two scanners having different rotation centers for scanning the measurement light,
wherein the correction unit corrects the curvature of the first tomographic image based on a positional difference between the rotation centers of the two scanners.

16. An image acquiring apparatus according to claim 12, wherein the correction unit shortens the first distance when a curvature of a retina of the eye to be inspected is measured to be larger than a predetermined value, to thereby acquire the tomographic image.

17. An image acquiring apparatus for acquiring a tomographic image of a retina of an eye to be inspected based on combined light of (a) return light from the eye to be inspected, which is irradiated with measurement light via an objective lens, and (b) reference light corresponding to the measurement light, the image acquiring apparatus comprising:
- an acquiring unit for acquiring a distance between the eye to be inspected and the objective lens, corresponding to the tomographic image;
- a calculation unit for calculating a curvature of the retina in the tomographic image based on the distance; and
- a correction unit for correcting the curvature of the tomographic image based on the distance.

18. An image acquiring apparatus according to claim 17, further comprising a determination unit for determining a region including a predetermined layer of the retina from the tomographic image,
- wherein the calculation unit calculates a curvature of the layer of the region based on the distance.

19. An image acquiring apparatus according to claim 17, further comprising a display control unit for controlling a display unit to superimpose and display a curve determined based on the curvature on the tomographic image.

20. An image acquiring apparatus according to claim 17, further comprising a display control unit for controlling a display unit to display curvatures calculated for a plurality of regions of the tomographic image as a map.

* * * * *